(12) United States Patent
Meade et al.

(10) Patent No.: US 7,507,745 B2
(45) Date of Patent: *Mar. 24, 2009

(54) PHARMACEUTICAL COMPOSITIONS BASED ON FLUORENECARBOXYLIC ACID ESTERS AND SOLUBLE TNF RECEPTOR FUSION PROTEINS

(75) Inventors: Christopher John Montague Meade, Maselheim (DE); Michel Pairet, Biberach (DE); Michael P. Pieper, Biberach (DE)

(73) Assignee: Boehringer Ingelheim International GmbH, Ingelheim (DE)

(*) Notice: Subject to any disclaimer, the term of this patent is extended or adjusted under 35 U.S.C. 154(b) by 79 days.

This patent is subject to a terminal disclaimer.

(21) Appl. No.: 11/038,658

(22) Filed: Jan. 18, 2005

(65) Prior Publication Data

US 2005/0186145 A1  Aug. 25, 2005

Related U.S. Application Data

(60) Provisional application No. 60/559,855, filed on Apr. 6, 2004.

(30) Foreign Application Priority Data

Feb. 20, 2004  (EP) .................... 04003896

(51) Int. Cl.
| | | |
|---|---|---|
| A01N 43/42 | (2006.01) | |
| A01N 43/46 | (2006.01) | |
| A61K 38/01 | (2006.01) | |
| A61K 9/10 | (2006.01) | |
| A61K 9/12 | (2006.01) | |
| A61K 9/14 | (2006.01) | |
| A61K 9/08 | (2006.01) | |
| A61K 9/48 | (2006.01) | |
| C07D 451/00 | (2006.01) | |
| C07D 451/04 | (2006.01) | |

(52) U.S. Cl. ............... 514/291; 514/2; 514/304; 546/91; 546/128; 424/45; 424/46; 424/489

(58) Field of Classification Search .......... 514/2, 514/291, 304; 546/89, 91, 128

See application file for complete search history.

(56) References Cited

U.S. PATENT DOCUMENTS

| | | | |
|---|---|---|---|
| 6,433,027 B1 | 8/2002 | Bozung et al. | |
| 6,790,856 B2 * | 9/2004 | Germeyer et al. | 514/291 |
| 2002/0115680 A1 | 8/2002 | Meissner et al. | |
| 2002/0119991 A1 | 8/2002 | Meissner et al. | |
| 2003/0199539 A1 | 10/2003 | Germeyer et al. | |
| 2003/0203928 A1 | 10/2003 | Germeyer et al. | |
| 2003/0207912 A1 | 11/2003 | Eickmeier et al. | |
| 2004/0053902 A1 * | 3/2004 | Smith | 514/171 |
| 2006/0189524 A1 | 8/2006 | Meade et al. | |

FOREIGN PATENT DOCUMENTS

| | | |
|---|---|---|
| WO | WO 00/69468 | 11/2000 |
| WO | 0200679 A2 | 1/2002 |
| WO | WO 02/32898 | 4/2002 |
| WO | WO 02/32899 | 4/2002 |
| WO | WO 02/096422 | 12/2002 |
| WO | WO 02/096423 | 12/2002 |
| WO | WO 03/064417 | 8/2003 |
| WO | WO 03/064418 | 8/2003 |
| WO | WO 03/064419 | 8/2003 |
| WO | 03072060 A2 | 9/2003 |

OTHER PUBLICATIONS

Halfhide et al. "Inhaled Bronchodilators for Cystic Fibrosis," Cochrane Database of Systematic Reviews, Oct. 2005, 4, CD003428 (abstract only).*
Lai et al. "Pediatric Allergic Rhinitis: Treatment," Immunology and allergy clinics of North America, May 2005, 25(2), pp. 283-299 (abstract only).*
Online Medical Dictionary definition of "antiallergics," accessed Apr. 4, 2007.*
Merck Manual Home Edition article entitled, "Allergic Reactions," accessed Apr. 5, 2007.*
Mikuls, T. D. et al. "TNF Blockade in the Treatment of Rheumatoid Arthritis: Infliximab versus Etanercept," Expert Opinion on Pharmacotherapy, 2001, 2(1), 75-84.*
Babu, K. et al; Soluble tumor necrosis factor alpha (TNF-Alpha) Receptor (Enbrel) as an effective therapeutic strategy in chronic severe asthma; Journal of Allergy and Clinical, Immunology, Mosby yearl book vol. 111 No. 2 Abstract Supplement Feb. 2003 p. S277.

(Continued)

Primary Examiner—Johann R Richter
Assistant Examiner—J. H. Alstrum-Acevedo
(74) Attorney, Agent, or Firm—Michael P. Morris; Mary-Ellen M. Devlin; Timothy X. Witkowski (57) ABSTRACT

The present invention relates to novel pharmaceutical compositions based on fluorene carboxylic acid ester derived anticholinergics of formula 1

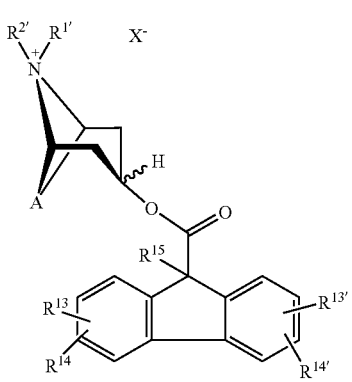

and soluble TNF receptor fusion proteins, processes for preparing them and their use in the treatment of respiratory diseases.

18 Claims, 1 Drawing Sheet

OTHER PUBLICATIONS

Renzetti, L. et al; Attenuation of allergic airway inflammation using RO 45-2081, A TNFR-IGGI fusion protein; FASEB Journal, Fed. of American Society for Experimentalbiology, Bethesda, vol. 9 No. 4 Mar. 10, 1995, p. A684.

Renzetti, I.m. et al; Pharmacological evidence for tumor necrosis factor as a mediator of allergic inflammation in the airways; Journal of Pharmacology and experimental therapeutics, american society for pharmacology AND; vol. 278 No. 2 Aug. 1996, pp. 847-853.

Gater, P.R. et al; Inhibition of Sephadex-induced lung injury in the rat by RO 45-2081, a tumor necrosis factor receptor fusion protein; American journal of respiratory cell and molecular biology, American lung association, vol. 14 No. 1 Jul. 1, 1996 pp. 454-460.

Renzetti, L.M. et al; RO 45-2081, a TNF receptor fusion protein, prevents inflammatory responses in the airways; Implammation Research, Birkhaeuser verlag, vol. 46 No. Supplement 2, 1997, pp. S143-S144.

Gater, P.R. et al; RO 45-2081, a TNF receptor fusion protein, prevents inflammatory responses in the airways; Agents and actions supplememts 1997 Switzerland, vol. 49, 1997, pp. 67-71.

T. R. Ulich, et al. "Intratracheal Administration of Endotoxin and Cytokines" American Journal of Pathology, vol. 142, No. 5, 1993, pp. 1335-1338 XP009033316.

Sorbera, L.A., et al. "Pegsunercept: Pegylated Soluble tumor Necrosis Factor Receptor Type 1", Drugs of the Future, 2003, 28(12), pp. 1182-1188 XP009033320.

A. Kokuludag, et al. "Serum Soluble Tumor Necrosis Factor Recepter Levels in Patients with Seasonal Allergic Rhinitis", J. Invest. Allergol. Clin. Immunol. 2001, vol. 11(1): pp. 46-48 XP009033321.

S. Yoshida, et al. "Elevation of Serum Soluble Tumour Necrosis Factor (TNF) receptor and IL-1 Receptor Antagonist Levels in Bronchial Asthma", Clin. Exp. Immunol. 1996. 106: 73-78 XP002287830.

T.T. Hansel, et al. "Tiotropium Bromide: A Novel Once-Daily Anticholinergic Bronchodilator for the Treatment of COPD", Drugs of Today, 2002, 38 (9): pp. 585-600 XP009022208.

de Boer; Pontential new drugs for therapy of chronic obstructive pulmonary disease; Expert Opinion on Investigational Drugs; vol. 12; No. 7, pp. 1067-1086; Ashley Publications.

* cited by examiner

FIG. 1.

PHARMACEUTICAL COMPOSITIONS BASED ON FLUORENECARBOXYLIC ACID ESTERS AND SOLUBLE TNF RECEPTOR FUSION PROTEINS

RELATED APPLICATIONS

Benefit of U.S. Provisional Application Ser. No. 60/559,855, filed on Apr. 6, 2004, and EP 04003896, filed on Feb. 20, 2004 is hereby claimed, which applications are incorporated herein in their entirety.

FIELD OF THE INVENTION

The present invention relates to novel pharmaceutical compositions based on fluorene carboxylic acid ester derived anticholinergics of formula 1 and soluble TNF receptor fusion proteins, processes for preparing them and their use in the treatment of respiratory diseases.

DESCRIPTION OF THE INVENTION

The present invention relates to novel pharmaceutical compositions based on anticholinergics and soluble TNF receptor fusion proteins, processes for preparing them and their use in the treatment of respiratory diseases.

Surprisingly, an unexpectedly beneficial therapeutic effect can be observed in the treatment of inflammatory and/or obstructive diseases of the respiratory tract if one or more, preferably one, anticholinergic is used with one or more, preferably one, soluble TNF receptor fusion protein.

In view of this synergistic effect the pharmaceutical combinations according to the invention can be used in smaller doses than would be the case with the individual compounds used in monotherapy in the usual way. The effects mentioned above may be observed both when the two active substances are administered simultaneously in a single active substance formulation and when they are administered successively in separate formulations. According to the invention, it is preferable to administer the two active substance ingredients simultaneously in a single formulation.

Within the scope of the present invention the term anticholinergics 1 denotes compounds of formula 1 wherein
A denotes a double-bonded group selected from among

X— denotes an anion with a single negative charge, preferably an anion selected from the group consisting of fluoride, chloride, bromide, iodide, sulphate, phosphate, methanesulphonate, nitrate, maleate, acetate, citrate, fumarate, tartrate, oxalate, succinate, benzoate and p-toluenesulphonate, more preferably chloride, bromide or methansulphonate, $R^{15}$ denotes hydrogen, hydroxy, methyl, ethyl, —$CF_3$, $CHF_2$ or fluorine;

$R^1$ and $R^2$ which may be identical or different denote $C_1$-$C_5$-alkyl which may optionally be substituted by $C_3$-$C_6$-cycloalkyl, hydroxy or halogen, or $R^1$ and $R^2$ together denote a —$C_3$-$C_5$-alkylene-bridge;

$R^{13}$, $R^{14}$, $R^{13'}$ and $R^{14'}$ which may be identical or different denote hydrogen, —$C_1$-$C_4$-alkyl,
—$C_1$-$C_4$-alkyloxy, hydroxy, —$CF_3$, —$CHF_2$, CN, $NO_2$ or halogen.

The compounds of formula 1 are disclosed for instance in WO 03/064419.

Particularly preferred within the combinations according to the invention are compounds of general formula 1, wherein A denotes a double-bonded group selected from among

X— denotes an anion selected from among chloride, bromide and methanesulphonate, preferably bromide;

$R^{15}$ denotes hydroxy, methyl or fluorine, preferably methyl or hydroxy;

$R^{1'}$ and $R^{2'}$ which may be identical or different represent methyl or ethyl, preferably methyl;

$R^{13}$, $R^{14}$, $R^{13'}$ and $R^{14'}$ which may be identical or different represent hydrogen, —$CF_3$,
—$CHF_2$ or fluorine, preferably hydrogen or fluorine.

Particularly preferred within the combinations according to the invention are compounds of general formula 1, wherein A denotes a double-bonded group selected from among

X— denotes bromide;
$R^{15}$ denotes hydroxy or methyl, preferably methyl;
$R^{1'}$ and $R^{2'}$ which may be identical or different represent methyl or ethyl, preferably methyl;
$R^{13}$, $R^{14}$, $R^{13'}$ and $R^{14'}$ which may be identical or different represent hydrogen or fluorine.

Of particular importance are those pharmaceutical compositions that contain the compound of formula 2 in combination with one of the following compounds 1:

scopine 9-methyl-fluorene-9-carboxylate methobromide (1a);
tropenol 9-fluoro-fluorene-9-carboxylate methobromide (1b);
scopine 9-hydroxy-fluorene-9-carboxylate methobromide (1c);
scopine 9-fluoro-fluorene-9-carboxylate methobromide (1d);
tropenol 9-methyl-fluorene-9-carboxylate methobromide (1e)
tropenol 9-hydroxy-fluorene-9-carboxylate methobromide (1f).

The pharmaceutical compositions according to the invention may contain the compounds of formula 1 optionally in the form of the individual optical isomers, mixtures of the individual enantiomers or racemates thereof.

Within the scope of the present invention, any reference to the compounds 1' is to be regarded as a reference to the pharmacologically active cation contained in the salts 1. These cations 1' are characterized by the general formula 1' wherein the various groups are defined as mentioned hereinbefore.

Any reference to compounds 1 naturally also includes a reference to the ingredients 1'.

Within the scope of the present invention, the term soluble TNF receptor fusion proteins (hereinafter 2 denotes compounds, which contain at least one TNF alpha binding site derived from a TNF alpha receptor (fused with other protein fragments such as the Fc portion of an immunoglobulin molecule) and which can be modified by pegylation. Of outstanding importance according to the invention are lenercept and etanercept. A particular preferred soluble TNF receptor fusion protein 2 is etanercept.

The pharmaceutical combinations of 1 and 2 according to the invention are preferably administered by inhalation. Suitable inhalable powders packed into suitable capsules (inhalettes) may be administered using suitable powder inhalers. The drug may also be inhaled using suitable solutions of the pharmaceutical combination consisting of 1 and 2.

In one aspect, therefore, the invention relates to a pharmaceutical composition which contains a combination of 1 and 2. In another aspect the present invention relates to a pharmaceutical composition which contains one or more salts 1 and one or more compounds 2, optionally in the form of their solvates or hydrates. Again, the active substances may be combined in a single preparation or contained in two separate formulations. Pharmaceutical compositions which contain the active substances 1 and 2 in a single preparation are preferred according to the invention.

In another aspect the present invention relates to a pharmaceutical composition which contains, in addition to therapeutically effective quantities of 1 and 22, a pharmaceutically acceptable excipient. In another aspect the present invention relates to a pharmaceutical composition which does not contain any pharmaceutically acceptable excipient in addition to therapeutically effective quantities of 1 and 2.

The present invention also relates to the use of 1 and 2 for preparing a pharmaceutical composition containing therapeutically effective quantities of 1 and 2 for treating inflammatory and/or obstructive diseases of the respiratory tract, particularly asthma or chronic obstructive pulmonary disease (COPD). Other diseases where the combination is useful are inflammatory diseases of the lung associated with fibrosis, such as cystic fibrosis and iodiopathic pulmonary fibrosis and inflammatory diseases of the upper airways such as rhinitis.

The present invention also relates to the use of 1 for preparing a pharmaceutical composition for treating inflammatory and/or obstructive diseases of the respiratory tract, particularly asthma or chronic obstructive pulmonary disease (COPD), characterized in that a therapeutically effective quantity of 2 is used as well.

The present invention also relates to the simultaneous or successive use of therapeutically effective doses of the combination of the above pharmaceutical compositions 1 and 2 for treating inflammatory and/or obstructive diseases of the respiratory tract, particularly asthma or chronic obstructive pulmonary disease (COPD) as well as allergic and non-allergic rhinitis, cystic fibrosis, and iodiopathic pulmonary fibrosis by simultaneous or successive administration.

In the active substance combinations of 1 and 2, ingredient 1 may be present in the form of enantiomers, mixtures of enantiomers or in the form of racemates, whilst ingredient 2 may be present as a glycosylated protein whereby the degree and type of glycosylation may be varied.

The proportions in which the two active substances 1 and 2 may be used in the active substance combinations according to the invention are variable. Active substances 1 and 2 may possibly be present in the form of their solvates or hydrates. Depending on the choice of the compounds 1 and 2, the weight ratios which may be used within the scope of the present invention vary on the basis of the different molecular weights of the various compounds and their different potencies.

As a rule, the pharmaceutical combinations according to the invention may contain compounds 1 and 2 in ratios by weight ranging from 1:2000 to 1:1, preferably from 1:1000 to 1:2. In the particularly preferred pharmaceutical combinations the weight ratios of 1 to 2 are most preferably in a range in which 1' and 2 are present in proportions of 1:250 to 1:3, more preferably from 1:100 to 1:5. For example, without restricting the scope of the invention thereto, preferred combinations of 1 and 2 according to the invention may contain 1' and anti TNF receptor fusion protein 2 in the following weight ratios: 1:200 1:100; 1:90; 1:85; 1:80; 1:75; 1:70; 1:65; 1:60; 1:55; 1:50; 1:49; 1:48; 1:47; 1:46; 1:45; 1:44; 1:43; 1:42; 1:41; 1:40; 1:39; 1:38; 1:37; 1:36; 1:35; 1:34; 1:33; 1:32; 1:31; 1:30; 1:29; 1:28; 1:27; 1:26; 1:25; 1:24; 1:23; 1:22; 1:21; 1:20; 1:19; 1:18; 1:17; 1:16; 1:15; 1:14; 1:13; 1:12; 1:11; 1:10; 1:9; 1:8; 1:7; 1:6; 1:5.

The pharmaceutical compositions according to the invention containing the combinations of 1 and 2 are normally administered so that 1 and 2 are present together in doses of 1 to 10000 μg, preferably from 10 to 5000 μg, more preferably from 100 to 5000 μg, better still from 1000 to 2000 kg per single dose. For example, combinations of 1 and 2 according to the invention contain a quantity of 1' and 2 such that the total dosage per single dose is about 200 μg, 205 μg, 210 μg, 215 μg, 220 μg, 225 μg, 230 μg, 235 μg, 240 μg, 245 μg, 250 μg, 255 μg, 260 μg, 265 μg, 270 μg, 275 μg, 280 μg, 285 μg, 290 μg, 295 μg, 300 μg, 305 μg, 310 μg, 315 μg, 320 μg, 325 μg, 3300 μg, 335 μg, 340 μg, 345 μg, 350 μg, 355 μg, 360 μg, 365 μg, 370 μg, 375 μg, 380 μg, 385 μg, 390 μg, 395 μg, 400 μg, 405 μg, 410 μg, 415 μg, 420 μg, 425 μg, 430 μg, 435 μg, 440 μg, 445 μg, 450 μg, 455 μg, 460 μg, 465 μg, 478 μg, 475 μg, 480 μg, 485 μg, 490 μg, 495 μg, 500 μg, 505 μg, 510 μg, 5515 μg, 520 μg, 525 μg, 530 μg, 535 μg, 540 μg, 545 μg, 550 μg, 555 μg, 560 μg, 565 μg, 570 μg, 575 μg, 580 μg, 585 μg, 590 μg, 595 μg, 600 μg, 605 μg, 610 μg, 615 μg, 6200 μg, 625 μg, 630 μg, 635 μg, 640 μg, 645 μg, 650 μg, 655 μg, 660 μg, 665 μg, 670 μg, 675 μg, 680 μg, 685 μg, 690 μg, 695 μg, 700 μg, 705 μg, 710 μg, 715 μg, 720 μg, 725 μg, 730 μg, 735 μg, 740 μg, 745 μg, 750 μg, 755 μg, 760 μg, 765 μg, 770 μg, 775 μg, 780 μg, 785 μg, 790 μg, 795 μg, 800 μg, 805 μg, 810 μg, 815 μg, 820 μg, 825 μg, 830 μg, 835 μg, 840 μg, 845 μg, 850 μg, 855 μg, 860 μg, 865 μg, 870 μg, 875 μg, 880 μg, 885 μg, 890 μg, 895 μg, 900 μg, 905 μg, 910 μg, 915 μg, 920 μg, 925 μg, 930 μg, 935 μg, 940 μg, 945 μg, 950 μg, 955 μg, 960 μg, 965 μg, 970 μg, 975 μg, 980 μg, 985 μg, 990 μg, 995 μg, 1000 μg, 1005 μg, 1010 μg, 1015 μg, 1020 μg, 1025 μg, 1030 μg, 1035 μg, 1040 μg, 1045 μg, 1050 μg, 1055 μg, 1060 μg, 1065 μg, 1070 μg, 1075 μg, 1080 μg, 1085 μg, 1090 μg, 1095 μg, 1100 μg, 1105 μg, 1110 μg, 1115 μg, 1120 μg, 1125 μg, 1130 μg, 1135 μg, 1140 μg, 1145 μg, 1150 μg, 1155 μg, 1160 μg, 1165 μg, 1170 μg, 1175 μg, 1180 μg, 1185 μg, 1190 μg, 1195 μg, 1200 μg, 1250 μg, 1300 μg, 1350 μg, 1400 μg, 1450 μg, 1500 μg, 1550 μg, 1600 μg, 1650 μg, 1700 μg, 1750 μg, 1800 μg, 1850 μg, 1900 μg, 1950 μg, 2000 μg, 2050 μg, 2100 μg, 2150 μg, 2200 μg or similar. The suggested dosages per single dose specified above are not to be regarded as being limited to the numerical values actually stated, but are intended as dosages which are disclosed by way of example. Of course, dosages which may fluctuate about the above-mentioned numerical values within a range of about +/−2.5 μg are also included in the values given above by way of example. In these dosage ranges, the active substances 1' and 2 may be present in the weight ratios given above.

For example, without restricting the scope of the invention thereto, the combinations of 1 and 2 according to the invention may contain a quantity of 1' and soluble TNF receptor fusion protein 2 such that, for each single dose, 20 μg of 1' and 50 μg of 2, 20 μg of 1' and 50 μg of 2, 20 μg of 1' and 100 μg of 2, 20 μg of 1' and 200 μg of 2, 20 μg of 1' and 300 μg of 2, 20 μg of 1' and 400 μg of 2, 20 μg of 1' and 500 μg of 2, 20 μg of 1' and 600 μg of 2, 20 μg of 1' and 700 μg of 2, 20 μg of 1' and 800 μg of 2, 20 μg of 1' and 900 μg of 2, 20 μg of 1' and 1000 μg of 2, 20 μg of 1' and 1500 μg of 2, 20 μg of 1' and 2000 μg of 2, 40 μg of 1' and 50 μg of 2, 40 μg of 1' and 1100 μg of 2, 40 μg of 1' and 200 μg of 2, 40 μg of 1' and 300 μg of 2, 40 μg of 1' and 400 μg of 2, 40 μg of 1' and 500 μg of 2, 40 μg of 1' and 600 μg of 2 or 40 μg of 1' and 700 μg of 2, 40 μg of 1' and 800 μg of 2, 40 μg of 1' and 900 μg of 2, 40 μg of 1' and 1000 μg of 2, 40 μg of 1' and 1500 μg of 2, 40 μg of 1' and 2000 μg of 2, 60 μg of 1' and 50 μg of 2, 60 μg of 1' and 100 μg of 2, 60 μg of 1' and 200 g of 2, 60 μg of 1' and 300 μg of 2, 60 μg of 1' and 400 μg of 2, 60 μg of 1' and 500 μg of 2, 60 μg of 1' and 600 μg of 2 or 60 μg of 1' and 700 μg of 2, 60 μg of 1' and 800 μg of 2, 60 μg of 1' and 900 μg of 2, 60 μg of 1' and 1000 μg of 2, 60 μg of 1' and 1500 μg of 2, 60 μg of 1' and 2000 μg of 2, 100 μg of 1' and 50 μg of 2, 100 μg of 1' and 100 μg of 2, 100 μg of 1' and 200 μg of 2, 100 μg of 1' and 300 μg of 2, 100 g of 1' and 400 μg of 2, 100 μg of 1' and 500 μg of 2, 100 μg of 1' and 600 μg of 2 or 100 μg of 1' and 700 μg of 2, 100 μg of 1' and 800 μg of 2, 100 μg of 1' and 900 μg of 2, 100 μg of 1' and 1000 μg of 2, 100 μg of 1' and 1500 μg of 2, 100 μg of 1' and 2000 μg of 2, 150 μg of 1' and 50 μg of 2, 150 μg of 1' and 100 μg of 2, 150 μg of 1' and 200 μg of 2, 150 μg of 1' and 300 μg of 2, 150 μg of 1' and 400 μg of 2, 150 μg of 1' and 500 μg of 2, 150 μg of 1' and 600 μg of 2 or 150 μg of 1' and 700 μg of 2, 150 μg of 1' and 800 μg of 2, 150 μg of 1' and 900 μg of 2, 150 μg of 1' and 1000 μg of 2, 150 μg of 1' and 1500 μg of 2, 150 μg of 1' and 2000 μg of 2, 200 μg of 1' and 50 μg of 2, 200 μg of 1' and 100 μg of 2, 200 μg of 1' and 200 μg of 2, 200 μg of 1' and 300 μg of 2, 200 μg of 1' and 400 μg of 2, 200 μg of 1' and 50 μg of 2, 200 μg of 1' and 600 μg of 2 or 200 μg of 1' and 700 μg of 2, 200 μg of 1' and 800 μg of 2, 200 μg of 1' and 900 μg of 2, 200 μg of 1' and 1000 g of 2, 200 μg of 1' and 1500 μg of 2, 200 μg of 1' and 2000 μg of 2 are administered.

From the aforementioned amounts of active cation 1' within the formulations according to the invention the total amount of salt 1 is readily calculable for the person of ordinary skill in the art, taking into account the mass of the anion of choice (e.g. bromide).

The aforementioned examples of possible doses applicable for the combinations according to the invention are to be understood as referring to doses per single application. However, these examples are not be understood as excluding the possibility of administering the combinations according to the invention multiple times. Depending on the medical need patients may receive also multiple inhalative applications. As an example patients may receive the combinations according to the invention for instance two or three times (e.g. two or three puffs with a powder inhaler, an MDI etc) in the morning of each treatment day. As the aforementioned dose examples are only to be understood as dose examples per single application (i.e. per puff) multiple application of the combinations according to the invention leads to multiple doses of the aforementioned examples. The application of the combositions according to the invention can be for instance once a day, or depending on the duration of action of the anticholinergic agent twice a day, or once every 2 or 3 days.

Moreover it is emphasised that the aforementioned dose examples are to be understood as examples of metered doses only. In other terms, the aforementioned dose examples are not to be understood as the effective doses of the combinations according to the invention that do in fact reach the lung. It is clear for the person of ordinary skill in the art that the delivered dose to the lung is generally lower than the metered dose of the administered active ingredients.

The active substance combinations of 1 and 2 according to the invention are preferably administered by inhalation. For this purpose, ingredients 1 and 2 have to be made available in forms suitable for inhalation. Inhalable preparations include inhalable powders and inhalable solutions. Inhalable powders according to the invention containing the combination of active substances 1 and 2 may consist of the active substances on their own or of a mixture of the active substances with physiologically acceptable excipients. Within the scope of the present invention, inhalable solutions also includes concentrates or sterile inhalable solutions ready for use in a nebuliser. The preparations according to the invention may contain the combination of active substances 1 and 2 either together in one formulation or in two separate formulations. These formulations which may be used within the scope of the present invention are described in more detail in the next part of the specification.

A) Inhalable Powder Containing the Combinations of Active Substances 1 and 2 According to the Invention:

The inhalable powders according to the invention may contain 1 and 2 either on their own or in admixture with suitable physiologically acceptable excipients.

If the active substances 1 and 2 are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose, trehalose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose, trehalose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum mass mean aerodynamic diameter of up to 250 µm, preferably between 10 and 150 µm, most preferably between 15 and 80 µm. It may sometimes seem appropriate to add finer excipient fractions with an mass mean aerodynamic diameter of 1 to 9 µm to the excipient mentioned above. These finer excipients are also selected from the group of possible excipients listed hereinbefore.

Finally, in order to prepare the inhalable powders according to the invention, active substance 1 and 2, preferably with an mass mean aerodynamic diameter of 0.5 to 10 µm, more preferably from 1 to 5 µm, is added to the excipient mixture. Processes for producing the inhalable powders according to the invention and finally mixing the ingredients together are known from the prior art. These processes may include, but are not limited to, spray drying or grinding and micronising. Particularly favoured are processes which protect the protein component from denaturation during the production of particles of the right size range to be suitable for inhalation. The inhalable powders according to the invention may be prepared and administered either in the form of a single powder mixture which contains both 1 and 2 or in the form of separate inhalable powders which contain only 1 or 2.

The inhalable powders according to the invention may be administered using inhalers known from the prior art. Inhalable powders according to the invention which contain a physiologically acceptable excipient in addition to 1 and 2 may be administered, for example, by means of inhalers which deliver a single dose from a supply using a measuring chamber as described in U.S. Pat. No. 4,570,630A, or by other means as described in DE 36 25 685 A. Preferably, the inhalable powders according to the invention which contain physiologically acceptable excipient in addition to 1 and 2 are packed into capsules (to produce so-called inhalettes) which are used in inhalers as described, for example, in WO 94/28958.

A particularly preferred inhaler for using the pharmaceutical combination according to the invention in inhalettes is shown in FIG. 1.

This inhaler (HANDIHALER®) for inhaling powdered pharmaceutical compositions from capsules is characterised by a housing 1 containing two windows 2, a deck 3 in which there are air inlet ports and which is provided with a screen 5 secured via a screen housing 4, an inhalation chamber 6 connected to the deck 3 on which there is a push button 9 provided with two sharpened pins 7 and movable counter to a spring 8, a mouthpiece 12 which is connected to the housing 1, the deck 3 and a cover 11 via a spindle 10 to enable it to be flipped open or shut and three holes 13 with diameters below 1 mm in the central region around the capsule chamber 6 and underneath the screen housing 4 and screen 5.

The main air flow enters the inhaler between deck 3 and base 1 near to the hinge. The deck has in this range a reduced width, which forms the entrance slit for the air. Then the flow reverses and enters the capsule chamber 6 through the inlet tube. The flow is then further conducted through the filter and filter holder to the mouthpiece. A small portion of the flow enters the device between mouthpiece and deck and flows then between filterholder and deck into the main stream. Due to production tolerances there is some uncertainty in this flow because of the actual width of the slit between filterholder and deck. In case of new or reworked tools the flow resistance of the inhaler may therefore be a little off the target value. To correct this deviation the deck has in the central region around the capsule chamber 6 and underneath the screen housing 4 and screen 5 three holes 13 with diameters below 1 mm. Through these holes 13 flows air from the base into the main air stream and reduces such slightly the flow resistance of the inhaler. The actual diameter of these holes 13 can be chosen by proper inserts in the tools so that the mean flow resistance can be made equal to the target value.

If the inhalable powders according to the invention are packed into capsules (inhalers) for the preferred use described above, the quantities packed into each capsule should be 1 to 30 mg, preferably 3 to 20 mg, more particularly 5 to 10 mg of inhalable powder per capsule. These capsules contain, according to the invention, either together or separately, the doses of 1' and 2 mentioned hereinbefore for each single dose.

B) Inhalable Solutions or Suspensions Containing the Combinations of Active Substances 1 and 2 According to the Invention:

In another preferred embodiement the active substance combination according to the invention is used in the form of inhalable solutions and suspensions. The solvent/suspending agent used may be aqueous or alcoholic, preferably ethanolic. The solvent/suspending agent may be water on its own or a mixture of water and ethanol. The relative proportion of ethanol compared with water is not limited (other than by the requirement that it not cause irreversible denaturation of the protein component of the mixture), but the maximum is up to 70 percent by volume, more particularly up to 60 percent by volume and most preferably up to 30 percent by volume. The remainder of the volume is made up of water. The solutions or suspensions containing 1 and 2, separately or together, are adjusted to a pH of 2 to 7, preferably 2 to 5, using suitable acids. The pH may be adjusted using acids selected from inorganic or organic acids. Examples of suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

According to the invention, the addition of editic acid (EDTA) or one of the known salts thereof, sodium edetate, as stabiliser or complexing agent is unnecessary in the present formulation. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred.

Co-solvents and/or other excipients may be added to the inhalable solutions according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the combination of active substances 1 and 2, only benzalkonium chloride and sodium edetate. In another preferred embodiment, no sodium edetate is present.

The inhalable solutions according to the invention are administered in particular using inhalers of the kind which are capable of nebulising a small amount of a liquid formulation in the therapeutic dose within a few seconds to produce an aerosol suitable for therapeutic inhalation. Within the scope of the present invention, preferred inhalers are those in which a quantity of less than 100 µL, preferably less than 50 µL, more preferably between 10 and 30 µL of active substance solution can be nebulised in preferably one spray action to form an aerosol with an mass mean aerodynamic diameter of less than 20 µm, preferably less than 10 µm, in such a way that the inhalable part of the aerosol corresponds to the therapeutically effective quantity.

An apparatus of this kind for delivery of a metered quantity of a liquid pharmaceutical composition for inhalation is described for example in International Patent Application WO 91/14468 and also in WO 97/12687 (cf. in particular FIGS. 6a and 6b). The nebulisers (devices) described therein are known by the name RESPIMAT®.

This nebuliser (RESPIMAT®) can advantageously be used to produce the inhalable aerosols according to the invention containing the combination of active substances 1 and 2. Because of its cylindrical shape and handy size of less than 9 to 15 cm long and 2 to 4 cm wide, this device can be carried at all times by the patient. The nebuliser sprays a defined volume of pharmaceutical formulation using high pressures through small nozzles so as to produce inhalable aerosols.

The preferred atomiser essentially consists of an upper housing part, a pump housing, a nozzle, a locking mechanism, a spring housing, a spring and a storage container, characterised by
- a pump housing which is secured in the upper housing part and which comprises at one end a nozzle body with the nozzle or nozzle arrangement,
- a hollow plunger with valve body,
- a power takeoff flange in which the hollow plunger is secured and which is located in the upper housing part,
- a locking mechanism situated in the upper housing part,
- a spring housing with the spring contained therein, which is rotatably mounted on the upper housing part by means of a rotary bearing,
- a lower housing part which is fitted onto the spring housing in the axial direction.

Figure 1:
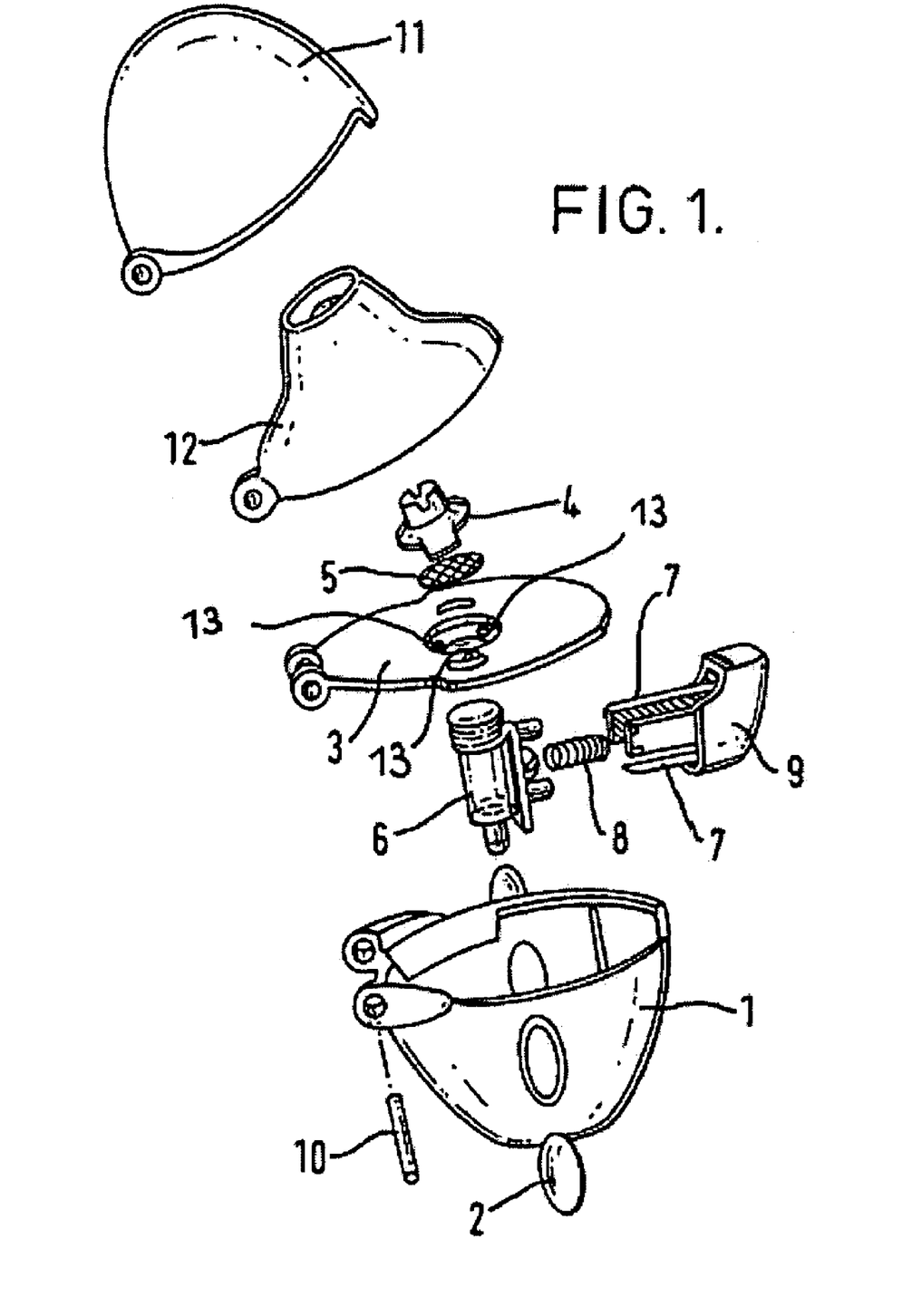

The hollow plunger with valve body corresponds to a device disclosed in WO 97/12687. It projects partially into the cylinder of the pump housing and is axially movable within the cylinder. Reference is made in particular to FIGS. 1 to 4, especially FIG. 3, and the relevant parts of the description. The hollow plunger with valve body exerts a pressure of 5 to 60 Mpa (about 50 to 600 bar), preferably 10 to 60 Mpa (about 100 to 600 bar) on the fluid, the measured amount of active substance solution, at its high pressure end at the moment when the spring is actuated. Volumes of 10 to 50 microlitres are preferred, while volumes of 10 to 20 microlitres are particularly preferred and a volume of 15 microlitres per spray is most particularly preferred.

The valve body is preferably mounted at the end of the hollow plunger facing the valve body.

The nozzle in the nozzle body is preferably microstructured, i.e. produced by microtechnology. Microstructured nozzle bodies are disclosed for example in WO-94/07607; reference is hereby made to the contents of this specification, particularly FIG. 1 therein and the associated description.

The nozzle body consists for example of two sheets of glass and/or silicon firmly joined together, at least one of which has one or more microstructured channels which connect the nozzle inlet end to the nozzle outlet end. At the nozzle outlet end there is at least one round or non-round opening 2 to 10 microns deep and 5 to 15 microns wide, the depth preferably being 4.5 to 6.5 microns while the length is preferably 7 to 9 microns. In the case of a plurality of nozzle openings, preferably two, the directions of spraying of the nozzles in the nozzle body may extend parallel to one another or may be inclined relative to one another in the direction of the nozzle opening. In a nozzle body with at least two nozzle openings at the outlet end the directions of spraying may be at an angle of 20 to 160° to one another, preferably 60 to 150°, most preferably 80 to 100°. The nozzle openings are preferably arranged at a spacing of 10 to 200 microns, more preferably at a spacing of 10 to 100 microns, most preferably 30 to 70 microns. Spacings of 50 microns are most preferred. The directions of spraying will therefore meet in the vicinity of the nozzle openings.

The liquid pharmaceutical preparation strikes the nozzle body with an entry pressure of up to 600 bar, preferably 200 to 300 bar, and is atomised into an inhalable aerosol through the nozzle openings. The preferred particle or droplet sizes of the aerosol are up to 20 microns, preferably 3 to 10 microns.

The locking mechanism contains a spring, preferably a cylindrical helical compression spring, as a store for the mechanical energy. The spring acts on the power takeoff flange as an actuating member the movement of which is determined by the position of a locking member. The travel of the power takeoff flange is precisely limited by an upper and lower stop. The spring is preferably biased, via a power step-up gear, e.g. a helical thrust gear, by an external torque which is produced when the upper housing part is rotated counter to the spring housing in the lower housing part. In this case, the upper housing part and the power takeoff flange have a single or multiple V-shaped gear.

The locking member with engaging locking surfaces is arranged in a ring around the power takeoff flange. It consists, for example, of a ring of plastic or metal which is inherently radially elastically deformable. The ring is arranged in a plane at right angles to the atomiser axis. After the biasing of the spring, the locking surfaces of the locking member move into the path of the power takeoff flange and prevent the spring from relaxing. The locking member is actuated by means of a button. The actuating button is connected or coupled to the locking member. In order to actuate the locking mechanism, the actuating button is moved parallel to the annular plane, preferably into the atomiser; this causes the deformable ring to deform in the annual plane. Details of the construction of the locking mechanism are given in WO 97/20590.

The lower housing part is pushed axially over the spring housing and covers the mounting, the drive of the spindle and the storage container for the fluid.

When the atomiser is actuated the upper housing part is rotated relative to the lower housing part, the lower housing part taking the spring housing with it. The spring is thereby compressed and biased by means of the helical thrust gear and the locking mechanism engages automatically. The angle of rotation is preferably a whole-number fraction of 360 degrees, e.g. 180 degrees. At the same time as the spring is biased, the power takeoff part in the upper housing part is moved along by a given distance, the hollow plunger is withdrawn inside the cylinder in the pump housing, as a result of which some of the fluid is sucked out of the storage container and into the high pressure chamber in front of the nozzle.

If desired, a number of exchangeable storage containers which contain the fluid to be atomised may be pushed into the atomiser one after another and used in succession. The storage container contains the aqueous aerosol preparation according to the invention.

The atomising process is initiated by pressing gently on the actuating button. As a result, the locking mechanism opens up the path for the power takeoff member. The biased spring pushes the plunger into the cylinder of the pump housing. The fluid leaves the nozzle of the atomiser in atomised form.

Further details of construction are disclosed in PCT Applications WO 97/12683 and WO 97/20590, to which reference is hereby made.

The components of the atomiser (nebuliser) are made of a material which is suitable for its purpose. The housing of the atomiser and, if its operation permits, other parts as well are preferably made of plastics, e.g. by injection moulding. For medicinal purposes, physiologically safe materials are used.

FIGS. 6a/b of WO 97/12687, show the nebuliser (RESPI-MAT®) which can advantageously be used for inhaling the aqueous aerosol preparations according to the invention.

FIG. 6a of WO 97/12687 shows a longitudinal section through the atomiser with the spring biased while FIG. 6b shows a longitudinal section through the atomiser with the spring relaxed.

The upper housing part (51) contains the pump housing (52) on the end of which is mounted the holder (53) for the atomiser nozzle. In the holder is the nozzle body (54) and a filter (55). The hollow plunger (57) fixed in the power takeoff flange (56) of the locking mechanism projects partially into the cylinder of the pump housing. At its end the hollow plunger carries the valve body (58). The hollow plunger is sealed off by means of the seal (59). Inside the upper housing part is the stop (60) on which the power takeoff flange abuts when the spring is relaxed. On the power takeoff flange is the stop (61) on which the power takeoff flange abuts when the spring is biased. After the biasing of the spring the locking member (62) moves between the stop (61) and a support (63) in the upper housing part. The actuating button (64) is connected to the locking member. The upper housing part ends in the mouthpiece (65) and is sealed off by means of the protective cover (66) which can be placed thereon.

The spring housing (67) with compression spring (68) is rotatably mounted on the upper housing part by means of the snap-in lugs (69) and rotary bearing. The lower housing part (70) is pushed over the spring housing. Inside the spring housing is the exchangeable storage container (71) for the fluid (72) which is to be atomised. The storage container is sealed off by the stopper (73) through which the hollow plunger projects into the storage container and is immersed at its end in the fluid (supply of active substance solution). The spindle (74) for the mechanical counter is mounted in the covering of the spring housing. At the end of the spindle facing the upper housing part is the drive pinion (75). The slider (76) sits on the spindle.

The nebuliser described above is suitable for nebulising the aerosol preparations according to the invention to produce an aerosol suitable for inhalation.

If the formulation according to the invention is nebulised using the method described above (RESPIMAT®) the quantity delivered should correspond to a defined quantity with a tolerance of not more than 25%, preferably 20% of this amount in at least 97%, preferably at least 98% of all operations of the inhaler (spray actuations). Preferably, between 5 and 30 mg of formulation, most preferably between 5 and 20 mg of formulation are delivered as a defined mass on each actuation.

However, the formulation according to the invention may also be nebulised by means of inhalers other than those described above, e.g. jet stream inhalers.

Accordingly, in a further aspect, the invention relates to pharmaceutical formulations in the form of inhalable solutions or suspensions as described above combined with a device suitable for administering these formulations, preferably in conjunction with the RESPIMAT®. Preferably, the invention relates to inhalable solutions or suspensions characterised by the combination of active substances 1 and 2 according to the invention in conjunction with the device known by the name RESPIMAT®. In addition, the present invention relates to the above-mentioned devices for inhalation, preferably the RESPIMAT®, characterised in that they contain the inhalable solutions or suspensions according to the invention as described hereinbefore.

The inhalable solutions or suspensions according to the invention may take the form of concentrates or sterile inhalable solutions or suspensions ready for use, as well as the above-mentioned solutions and suspensions designed for use in a RESPIMAT®. Formulations ready for use may be produced from the concentrates, for example, by the addition of isotonic saline solutions. Sterile formulations ready for use may be administered using energy-operated fixed or portable nebulisers which produce inhalable aerosols by means of ultrasound or compressed air by the Venturi principle or other principles.

Accordingly, in another aspect, the present invention relates to pharmaceutical compositions in the form of inhalable solutions or suspensions as described hereinbefore which take the form of concentrates or sterile formulations ready for use, combined with a device suitable for administering these solutions, characterised in that the device is an energy-operated free-standing or portable nebuliser which produces inhalable aerosols by means of ultrasound or compressed air by the Venturi principle or other methods.

The Examples which follow serve to illustrate the present invention in more detail without restricting the scope of the invention to the following embodiments by way of example.

EXAMPLES OF FORMULATIONS

A Inhalable Powders:

| Ingredients | µg per capsule |
|---|---|
| 1) | |
| 1a (bromide) | 75 |
| etanercept | 200 |
| lactose | 4778.3 |
| total | 5000 |
| 2) | |
| 1a (bromide) | 100 |
| etanercept | 125 |
| lactose | 4775 |
| total | 5000 |
| 3) | |
| 1a (bromide) | 100 |
| etanercept | 250 |
| lactose | 4650 |
| total | 5000 |
| 4) | |

-continued

| Ingredients | µg per capsule |
|---|---|
| 1a (bromide) | 50 |
| etanercept | 250 |
| trehalose | 4700 |
| total | 5000 |
| 5) | |
| 1a (bromide) | 50 |
| etanercept | 495 |
| trehalose | 4455 |
| total | 5000 |
| 6) | |
| 1a (bromide) | 75 |
| etanercept | 400 |
| lactose | 4525 |
| total | 5000 |
| 7) | |
| 1d (bromide) | 75 |
| etanercept | 200 |
| lactose | 4778.3 |
| total | 5000 |
| 8) | |
| 1b (bromide) | 100 |
| etanercept | 125 |
| lactose | 4775 |
| total | 5000 |
| 9) | |
| 1d (bromide) | 100 |
| etanercept | 250 |
| lactose | 4650 |
| total | 5000 |
| 10) | |
| 1b (bromide) | 50 |
| etanercept | 250 |
| trehalose | 4700 |
| total | 5000 |
| 11) | |
| 1c (bromide) | 50 |
| etanercept | 495 |
| trehalose | 4455 |
| total | 5000 |
| 12) | |
| 1b (bromide) | 75 |
| etanercept | 400 |
| lactose | 4525 |
| total | 5000 |

What is claimed is:

1. A pharmaceutical composition, comprising one or more anticholinergics of formula 1 wherein

A denotes a group selected from among

X—denotes an anion with a single negative charge which is selected from the group consisting of fluoride, chloride, bromide, iodide, sulphate, phosphate, methanesulphonate, nitrate, maleate, acetate, citrate, fumarate, tartrate, oxalate, succinate, benzoate and p-toluenesulphonate, $R^{15}$ denotes hydrogen, hydroxy, methyl, ethyl, —$CF_3$, $CHF_2$ or fluorine;

$R^{1'}$ and $R^{2'}$ which may be identical or different denote $C_1$-$C_5$-alkyl which may optionally be substituted by $C_3$-$C_6$-cycloalkyl, hydroxy or halogen, or $R^{1'}$ and $R^{2'}$ together denote a —$C_3$-$C_5$-alkylene-bridge;

$R^{13}$, $R^{14}$, $R^{13'}$ and $R^{14'}$ which may be identical or different denote hydrogen, —$C_1$-$C_4$-alkyl, —$C_1$-$C_4$-alkyloxy, hydroxy, —$CF_3$, —$CHF_2$, CN, $NO_2$ or halogen, or pharmacologically acceptable acid addition salts thereof, in combination with one or more soluble TNF receptor fusion proteins (2).

2. The pharmaceutical composition according to claim 1, wherein the soluble TNF receptor fusion protein 2 is etanercept or lenercept.

3. The pharmaceutical composition according to claim 2, wherein the soluble TNF receptor fusion protein 2 is etanercept.

4. The pharmaceutical composition according to claim 1, wherein the active substances 1 and 2 are present either together in a single formulation or in two separate formulations.

5. The pharmaceutical composition according to claim 1, wherein the weight ratios of the active substances 1 to 2 are in the range from 1:2000 to 1:1.

6. The pharmaceutical composition according to claim 4 wherein a single administration corresponds to a dose of the active substance combination 1 and 2 of 1 to 10000 µg.

7. The pharmaceutical composition according to claim 1, which is in a form of a formulation suitable for inhalation.

8. The pharmaceutical composition according to claim 7, wherein the formulation is selected from the group consisting of inhalable powders, inhalable solutions and inhalable suspensions.

9. The pharmaceutical composition according to claim 8, wherein the inhalable powder comprises active substances 1 and 2 in admixture with suitable physiologically acceptable excipients selected from the group consisting of monosaccharides, disaccharides, oligo- and polysaccharides, polyalcohols, salts, and mixtures thereof.

10. The pharmaceutical composition according to claim 9, wherein the excipient has a maximum mass mean aerodynamic diameter of up to 250 µm.

11. The pharmaceutical composition according to claim 9, wherein the inhalable powder is in a capsule.

12. The pharmaceutical composition according to claim 8, wherein the inhalable powder contains only the active substances 1 and 2 as its ingredients.

13. The pharmaceutical composition according to claim 8, wherein the inhalable solution or suspension contains water, ethanol or a mixture of ethanol and water as solvent.

14. The pharmaceutical composition according to claim 13, wherein the inhalable solution or suspension has a pH of 2-7.

15. The pharmaceutical composition according to claim 11, wherein the capsule is administered in an inhaler.

16. The pharmaceutical composition according to claim 13, wherein the inhalable solution or suspension is administered by nebulizing in a suitable inhaler.

17. The pharmaceutical composition according to claim 1, further comprising one or more pharmaceutically acceptable excipients.

18. A method of treating COPD or asthma comprising administering to a patient in need thereof the pharmaceutical composition according to claim 1.

* * * * *